US011253375B2

(12) United States Patent
Siccardi et al.

(10) Patent No.: US 11,253,375 B2
(45) Date of Patent: Feb. 22, 2022

(54) DEVICE FOR POSITIONING A RESURFACING PROSTHESIS AND METHOD OF ASSEMBLING SAID DEVICE

(71) Applicant: MEDACTA INTERNATIONAL S.A., Castel San Pietro (CH)

(72) Inventors: Francesco Siccardi, Castel San Pietro (CH); Massimiliano Bernardoni, Castel San Pietro (CH); Sami Abdel Jaber, Castel San Pietro (CH)

(73) Assignee: MEDACTA INTERNATIONAL S.A., Castel San Pietro (CH)

( * ) Notice: Subject to any disclaimer, the term of this patent is extended or adjusted under 35 U.S.C. 154(b) by 188 days.

(21) Appl. No.: 16/493,637

(22) PCT Filed: Mar. 12, 2018

(86) PCT No.: PCT/IB2018/051622
§ 371 (c)(1),
(2) Date: Sep. 12, 2019

(87) PCT Pub. No.: WO2018/167639
PCT Pub. Date: Sep. 20, 2018

(65) Prior Publication Data
US 2020/0000609 A1 Jan. 2, 2020

(30) Foreign Application Priority Data
Mar. 15, 2017 (IT) .................. 102017000028701

(51) Int. Cl.
*A61F 2/46* (2006.01)
*A61F 2/30* (2006.01)
(52) U.S. Cl.
CPC .......... *A61F 2/4609* (2013.01); *A61F 2/4612* (2013.01); *A61F 2/4603* (2013.01);
(Continued)

(58) Field of Classification Search
CPC .... A61F 2/4609; A61F 2/4612; A61F 2/4603; A61F 2/46; A61F 2002/4627; A61F 2002/4625
See application file for complete search history.

(56) References Cited

U.S. PATENT DOCUMENTS 5,108,445 A * 4/1992 Ashby .................. A61F 2/4637
623/22.29
2006/0058885 A1 3/2006 Wozencroft
(Continued)

FOREIGN PATENT DOCUMENTS

EP 2977028 A1 1/2016

OTHER PUBLICATIONS

International Search Report for PCT/IB2018/051622, dated Jun. 21, 2018, 3 pages.

*Primary Examiner* — Amy R Sipp
(74) *Attorney, Agent, or Firm* — Meunier Carlin & Curfman LLC

(57) ABSTRACT

Disclosed is a device for positioning a resurfacing prosthesis, including: a gripping and handling instrument for a main body of a resurfacing prosthesis; a connecting body, interposed between said gripping and handling instrument and said main body of said resurfacing prosthesis and suitable to connect them; a coupler which secures said connecting body to said main body, said coupler comprising: a plurality of bonding elements adapted to be interlocked, in an irremovable manner, in respective recesses provided in said connecting body; and a shear releaser, interposed between said main body of said resurfacing prosthesis and said connecting body, adapted to detach said connecting body from said main body. Other aspects are described and claimed.

10 Claims, 6 Drawing Sheets

(52) U.S. Cl.
CPC .............. *A61F 2002/30561* (2013.01); *A61F 2002/4631* (2013.01)

(56) References Cited

U.S. PATENT DOCUMENTS

| | | | |
|---|---|---|---|
| 2011/0153025 A1* | 6/2011 | McMinn ............... | B29C 43/003 623/20.32 |
| 2012/0150310 A1* | 6/2012 | Taylor ...................... | A61F 2/34 623/22.21 |
| 2014/0309749 A1* | 10/2014 | Taylor ...................... | A61F 2/34 623/22.32 |
| 2014/0336776 A1* | 11/2014 | Taylor ...................... | A61F 2/34 623/22.21 |

* cited by examiner

DEVICE FOR POSITIONING A RESURFACING PROSTHESIS AND METHOD OF ASSEMBLING SAID DEVICE

The present application is a National Phase Entry of PCT International Application No. PCT/IB2018/051622, which was filed on Mar. 12, 2018, and which claims priority to application Ser. No. 10/201,7000028701 filed in Italy on Mar. 15, 2017, the contents of which are hereby incorporated by reference.

The present invention relates to a device for positioning a resurfacing prosthesis and a related method of assembly.

Resurfacing or surface prosthesis refers to that type of implant that provides, in fact, the resurfacing and not the replacement of the worn joint bone.

This type of prosthesis has been developed precisely because lately more and more young people resort to it: this implant provides great advantages to the patient, especially if young, because it allows a more active life and a greater sparing of the patient's bone tissue (only the damaged surfaces are removed) during the joint replacement surgery procedure, compared to traditional prostheses.

Within the context of joint prosthetics, for example of the hip or the shoulder, resurfacing prosthesis is a solution which allows the joint to maintain its natural degrees of freedom of movement and likewise allows the sparing of a large amount of bone tissue for any subsequent operations.

In the case of hip arthroplasty, the resurfacing prosthesis has a femoral—or or humeral in the case of shoulder arthroplasty—head component characterised by a large diameter compared to conventional femoral or humeral heads of total hip or shoulder prostheses. Consequently, the respective acetabular cup or glenoid cavity, which for convenience will hereinafter be referred to as the main prosthesis component, which must be positioned within the operative site, must have limited thickness, to minimize the necessary reaming or boring and spare as much bone tissue as possible. Hence the difficulty in creating solutions for gripping the prosthesis component with a plate which provides an ideal grip for positioning the component within the area of operation, in order to move it considering the high friction and, in the end, impact it in situ and release it.

More generally, the system for the coupling between the acetabular cup/glenoid cavity and the impaction plate is particularly relevant even in arthroplasty operations that require processing and replacement of the acetabulum or glenoid cavity. Impaction plate refers to the instrument through which a connection is made between the acetabular cup/glenoid cavity and the instrument used by the surgeon for positioning and impacting (impaction handle). It is essential to establish an integral system between the acetabular cup/glenoid cavity and the plate, which has sufficient rigidity to enable the positioning of the acetabular cup/glenoid cavity within the processed acetabulum/glenoid seat, and make any orientation adjustments, considering a possible resistance dictated by the trabecular bone structures in contact with a structure that is highly irregular from the point of view of the roughness or surface geometry, such as the outer surface of the acetabular cup/glenoid cavity.

Several types of systems for coupling and positioning the acetabular/glenoid component exist on the market. Currently, several systems of coupling between the acetabular cup/glenoid cavity and the plate are used in the field of resurfacing prostheses. Some of these systems are toothed plates that have teeth, which can be actuated by the impaction handle, suitable for temporarily gripping corresponding elements placed on the prosthesis component. These teeth release the element to which they cling as a result of a reverse movement of the impaction handle. Other systems are, for example, wiring systems with metal cables, which are passed through special cavities formed in the plate and in the component to bind the two elements together. Furthermore, suction systems can be provided which, by providing pneumatic vacuum, keep the two bodies connected until pressure reversal.

The main problems of the known systems are due to the coupling system, which has connections that are unstable or, on the other hand, excessively rigid or accompanied by fragility.

Very often it is necessary to use two different plates, one for positioning and one for impacting the prosthesis component within the seat.

In the case of coupling systems for a resurfacing acetabular/glenoid component, a further difficulty is the small size of the thicknesses involved. The bending radii of the prostheses are much larger as it is sought to leave the physiognomy of the joint unaltered by coating the femoral or humeral head with a special material.

Given the considerable characteristic size of the radii, it is often not possible to arrange appropriate seats in the patient's joint. For this reason, the trend is to limit the thickness of the prostheses in order to limit the invasiveness of the implant in the patient's bone structure as much as possible.

Historically, metal-to-metal coupling has guaranteed stability and durability, however entailing considerable risks to the health of the patient, as has been established in more recent years, such as metallosis. To overcome said drawback, modern surgery has decided to make use of so-called "metal-on-polyethylene" prostheses, where the first and the second material face each other, avoiding the harmful metal-to-metal interaction, as was previously the case. However, this new type of prosthesis requires geometrical structures that make it difficult to create undercuts or housings in the prosthesis through which the latter can be engaged by the plate and then impact into the acetabulum of the patient.

It is therefore necessary to find technological solutions, which allow a stable connection between the plate and the prosthesis component to ensure correct positioning and orientation in the operative site.

It is essential that there is a stable and solid coupling between the impaction plate and the main prosthesis component, to prevent misalignments or positioning problems during impaction.

The object of the present invention is to provide a device for positioning a resurfacing prosthesis, which overcomes the above-mentioned drawbacks of the prior art.

An object of the present invention is to provide a device for positioning a resurfacing prosthesis, which ensures greater stability to the connection between the impaction plate and the main prosthesis component during impaction, to allow correct installation of the prosthesis and easy positioning thereof without risks to the patient.

A further object of the present invention is to provide a device for positioning a resurfacing prosthesis, which also ensures a quick and simple disengagement between the impaction plate and the prosthesis component, thus preventing accidental misalignments of the prosthesis itself within the operative site.

The device for positioning a resurfacing prosthesis, object of the present invention, also guarantees a simple and easy use by the surgeon who must be able to couple the impaction plate to the main prosthesis component in a quick manner and by using one hand, minimizing manual intervention by the surgeon in the operative phase.

Lastly, an object of the present invention is therefore to provide a method of assembling a device for the positioning of a resurfacing prosthesis, which allows a quick and stable coupling between the impaction plate and the prosthesis component and an equally fast release of one element from the other.

These and other objects are substantially achieved by means of a device for positioning a resurfacing prosthesis and a method of assembling said device as described in one or more of the accompanying claims.

Further advantageous features are set forth in the dependent claims.

The present invention will become more apparent from the detailed description that follows, with reference to the accompanying drawings provided purely by way of example, in which.

Figure 1:
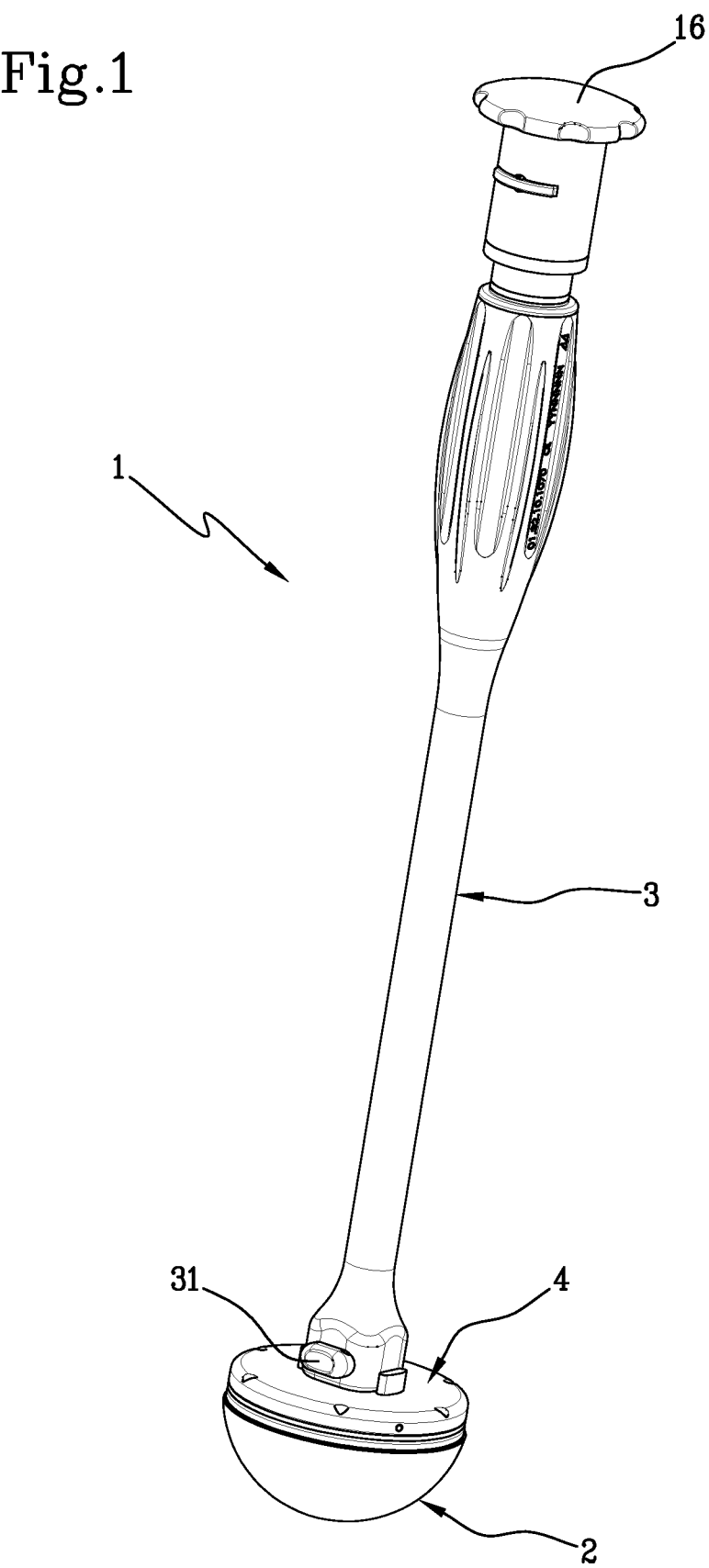
FIG. 1 is a perspective view of a device for positioning an impaction prosthesis secured to a main body of said prosthesis, in accordance with the present invention.
Figure 2:
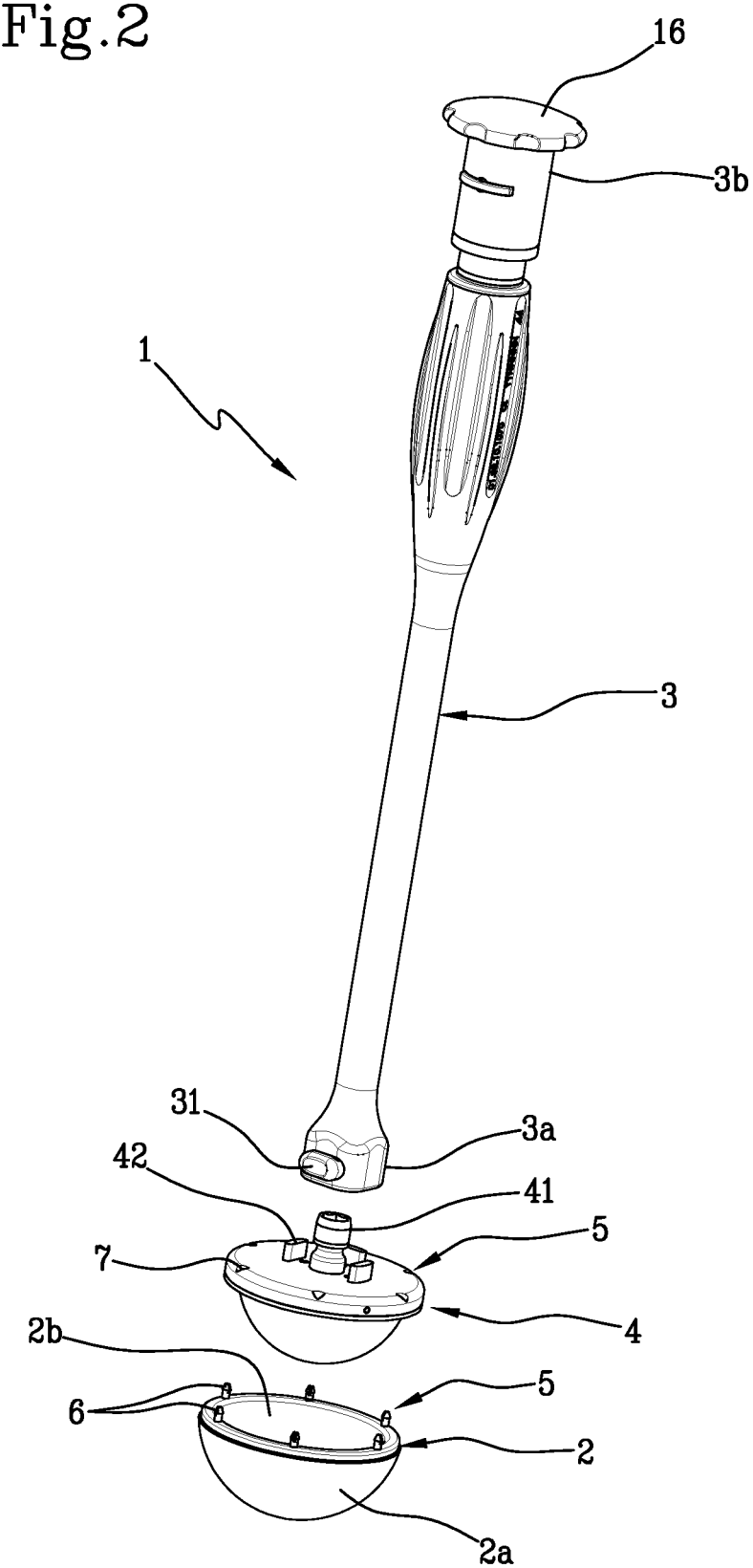
FIG. 2 is a partially exploded perspective view of what is shown in FIG. 1.
Figure 3A:
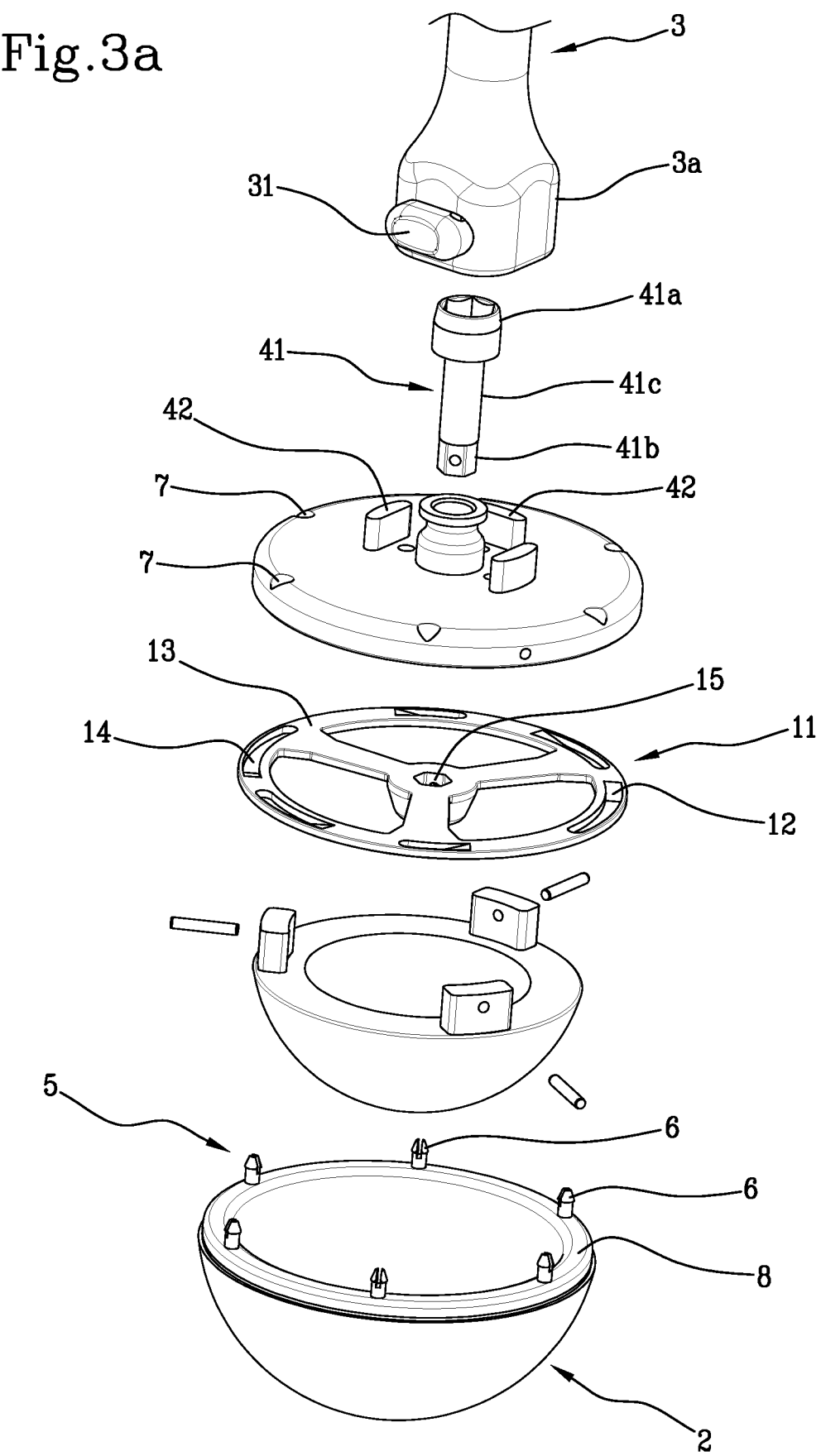
FIG. 3a is a first exploded perspective view of a portion of the device object of the present invention.
Figure 3B:
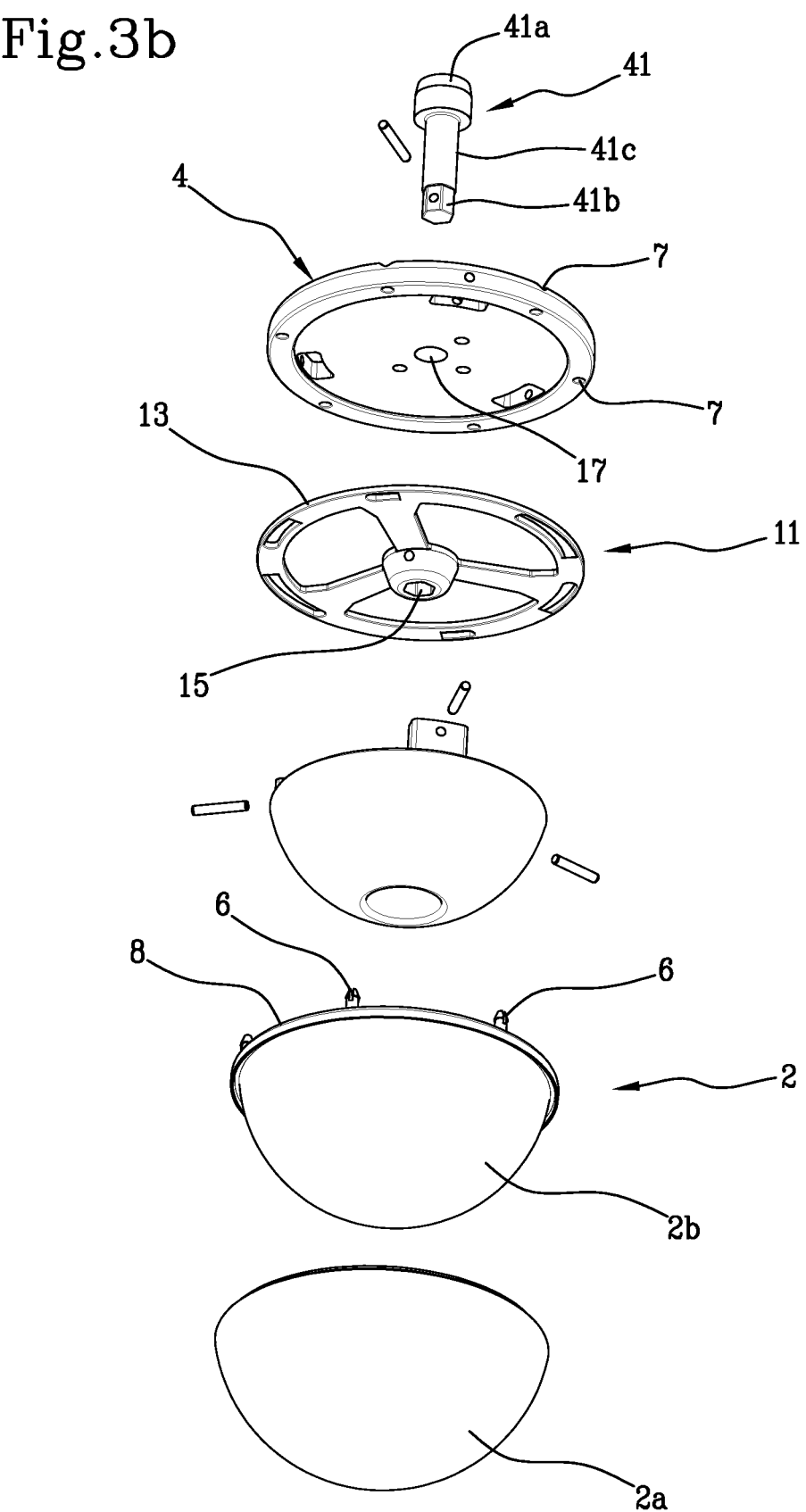
FIG. 3b is a second exploded perspective view of a portion of the device object of the present invention.
Figure 4:
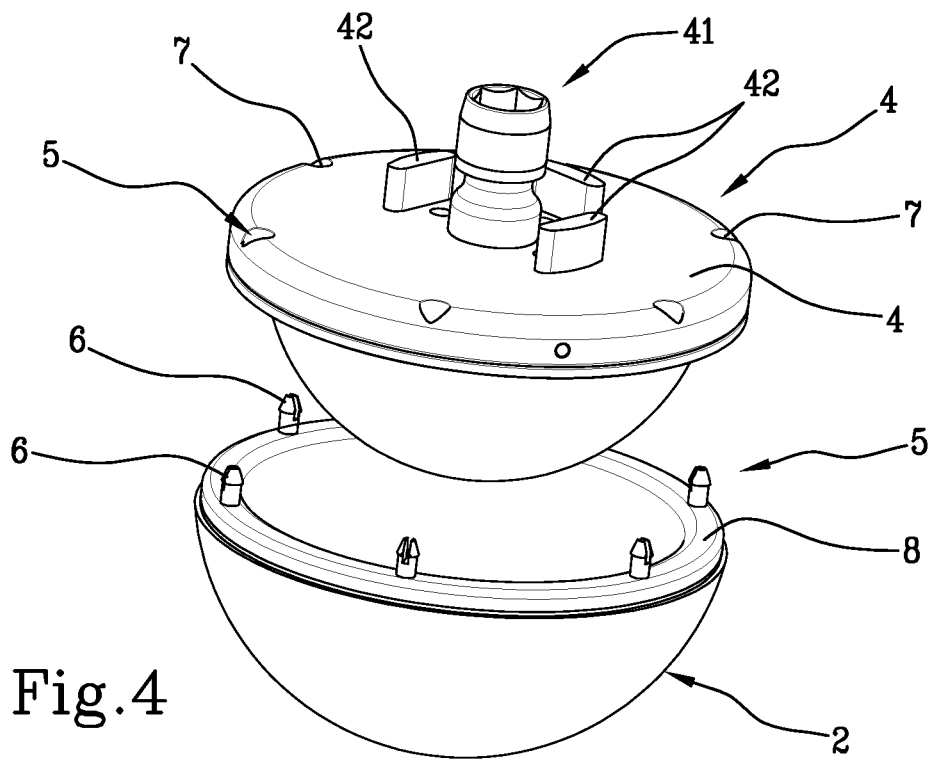
FIG. 4 is a perspective view of a connecting body of the positioning device object of the present invention, coupled to a main body of a resurfacing prosthesis.

In the attached figures, the numeral 1 indicates a device for positioning a resurfacing prosthesis in accordance with the present invention.

The attached figures show a hip resurfacing prosthesis purely by way of non-limiting example.

By way of illustrative and non-limiting example, the following description will make explicit reference to a resurfacing prosthesis for the hip joint.

The device object of the present invention is however also easily achievable for a shoulder resurfacing prosthesis.

These prostheses substantially comprise two distinct and mutually interacting elements capable of mimicking the patient's native joint. A first element of said prosthetic system is the acetabular cup (or main prosthesis body, as it will be referred to in the remainder of the present specification), which is adapted to be integrally coupled to the patient's iliac bone structure, and a second element designated as the femoral stem, which is adapted to be integrally coupled to the femur.

The acetabular cup or main body 2 has a substantially hemispherical, hollow shape and comprises an outer portion 2a adapted to mate with the patient's bone structure. This outer portion 2a is made of trabecular metal, generally titanium alloy Ti-4Al-6V. Said trabecular metal, known in the state of the art, has the ability to maximize the osseointegration of the acetabular cup in the patient's bone structure. An inner portion 2b, called insert, made of plastic material, usually polyethylene, can be seen inside said outer portion. Said inner portion 2b is made integral with the outer portion by high-pressure compression moulding. Thanks to said moulding process, the polyethylene is forced to adhere to the trabecular structure of the outer portion, the outer trabecular metal portion being formed in one body with the inner polyethylene portion.

The positioning device 1 object of the present invention comprises a gripping and handling instrument 3 for a main body 2 of a resurfacing prosthesis, as previously described.

This gripping and handling instrument 3 can be, for example, in the form of a handle or handpiece, which allows the surgeon to have a firm grip.

A connecting body 4, which engages the main body 2 of the prosthesis by means of suitable coupling means, is interposed between the gripping and handling instrument 3 and the main body 2 of the resurfacing prosthesis.

The gripping and handling instrument 3, in turn, adheres to the connecting body 4 via a shaft coupling 41, or other known type of mechanism.

The connecting body 4, represented in the form of a plate in the attached figures, has a central circular seat passing through the connection to said shaft coupling 41.

The gripping and handling instrument 3 is provided, at a first end 3a, with a trigger button 31, which allows the movement of a gripping mechanism, which thus connects to the shaft coupling 41. By acting on the button 31, the seat designed to receive the corresponding shaft coupling 41 of the connecting body 4 and located at one end 3a of the instrument 3, is freed, thus allowing access thereto. By releasing the button 31, a special guillotine lock mechanism (not shown) engages a respective seat provided on the shaft 41 of the connecting body 4, preventing relative translation in the axial direction between the gripping and handling instrument 3 and the connecting body 4.

A plurality of projections 42, preferably three, are accommodated within the seat designed to receive the shaft 41. The shape of said projections 42 and their position are such as to prevent relative rotation between the gripping and handling instrument 3 and the connecting body 4.

The coupling means 5 between the main body 2 and the connecting body 4 comprise a plurality of bonding elements 6 adapted to be interlocked, in an irremovable manner, in respective recesses 7 provided in the connecting body 4.

The main body 2 has an upper edge or lip 8, which defines the top of the portion of the prosthesis that faces the outside of the patient's iliac bone structure. This lip 8, once positioned within the patient, must be smooth, levelled and free of projections.

However, in an initial phase, prior to the actual implementation of the prosthesis itself, the main body 2 has a lip 8 provided with a plurality of bonding elements 6 projecting in the axial direction.

These bonding elements 6 preferably comprise a plurality of pins extending upwards from the lip 8 of the main body 2. They can be co-moulded with the inner portion of the main body 2, hence with the insert, made of plastic material, usually polyethylene. Alternatively, said plurality of pins can be formed in one piece with the inner portion of the main body 2.

Advantageously, these pins 6 have a change in diameter along their axial length and at least one undercut 9, adapted to abut against an edge 10 of the respective recess 7 of the connecting body 4, to which the pin 6 couples.

Figure 6:
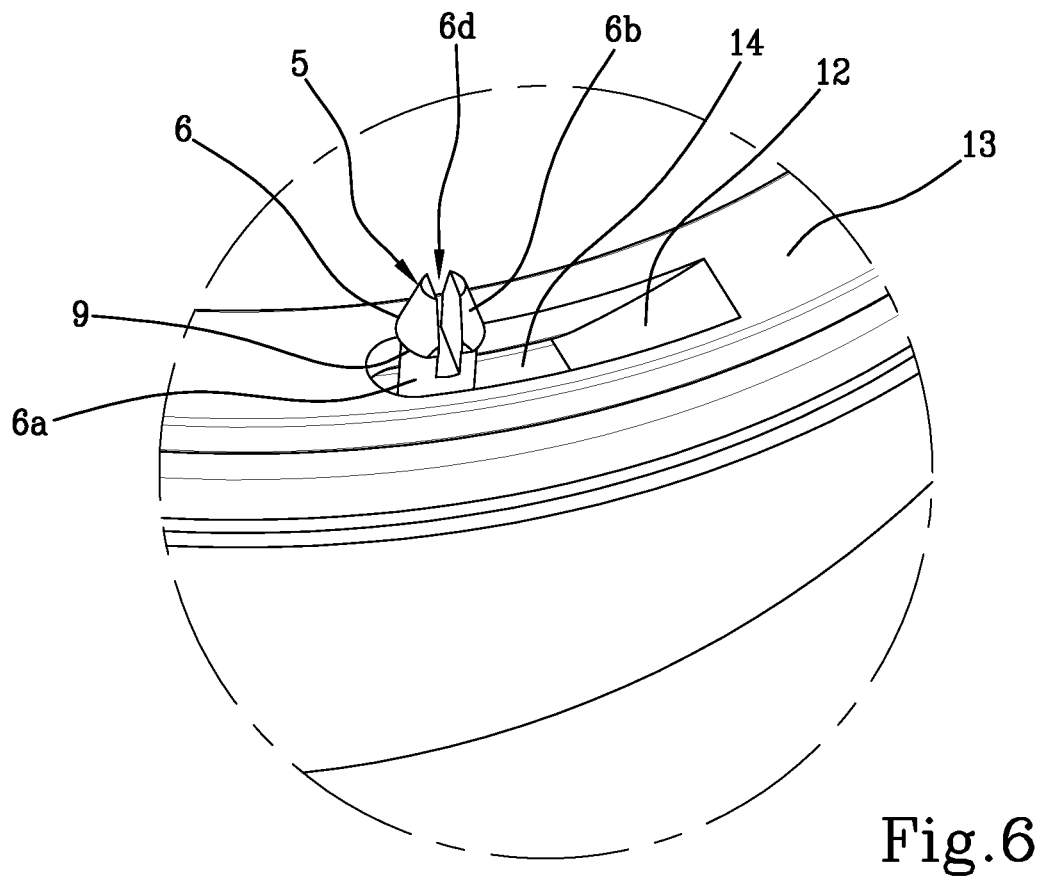
FIG. 6 is an enlargement of a detail of a coupling means and of the corresponding releasing means.
Figure 7:
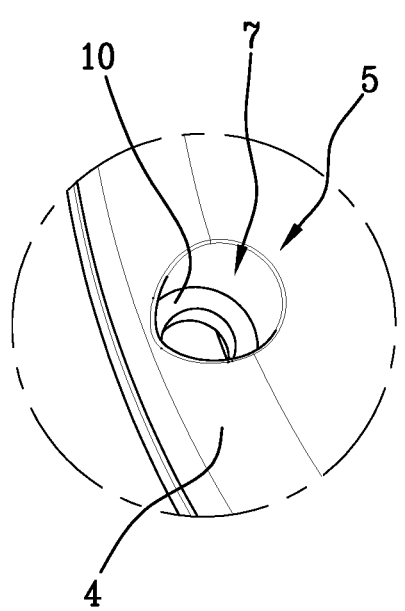
FIG. 7 is a detail of a recess provided in the connecting body.
Figure 8:
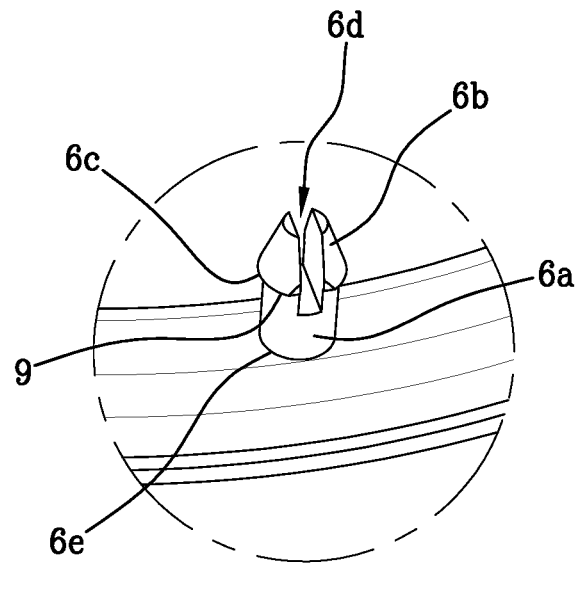
FIG. 8 is a detail of a bonding element of the positioning device.

Specifically, as shown in FIG. 6 or 8, each pin 6 has a cylindrical shank 6a and a conical head 6b having a larger base 6c with a greater diameter than the diameter of the cylindrical shank 6a, and an axial slot 6d, which from the tip of the conical head 6c penetrates at least partially inside the conical head in the axial direction, to allow deformation of the pin 6 during its insertion inside the respective recess 7 and facilitate the coupling between the connecting body 4 and the main body 2.

Each recess 7 has a through hole preferably surrounded by an annular edge 10, against which the undercut 9 of the pin 6 abuts.

The positioning device 1 further comprises releasing means 11 adapted to detach the connecting body 4 from the main body 2.

These releasing means 11 are preferably shear releasing means comprising a plurality of blades 12 that can be operated by rotation of the gripping and handling instrument 3 or a part thereof, as will be described below.

The releasing means 11 act directly on the bonding elements 6 to separate them from the main body 2 of the prosthesis by cutting the pins 6 directly at their respective base 6e.

This clean cut allows to obtain a prosthesis without unnecessary projections that, on the contrary, would be absolutely detrimental. The lip 8 of the main body 2 is thus completely smooth.

Advantageously, the releasing means 11 are interposed between the main body 2 of the resurfacing prosthesis and the connecting body 4.

Figure 5:
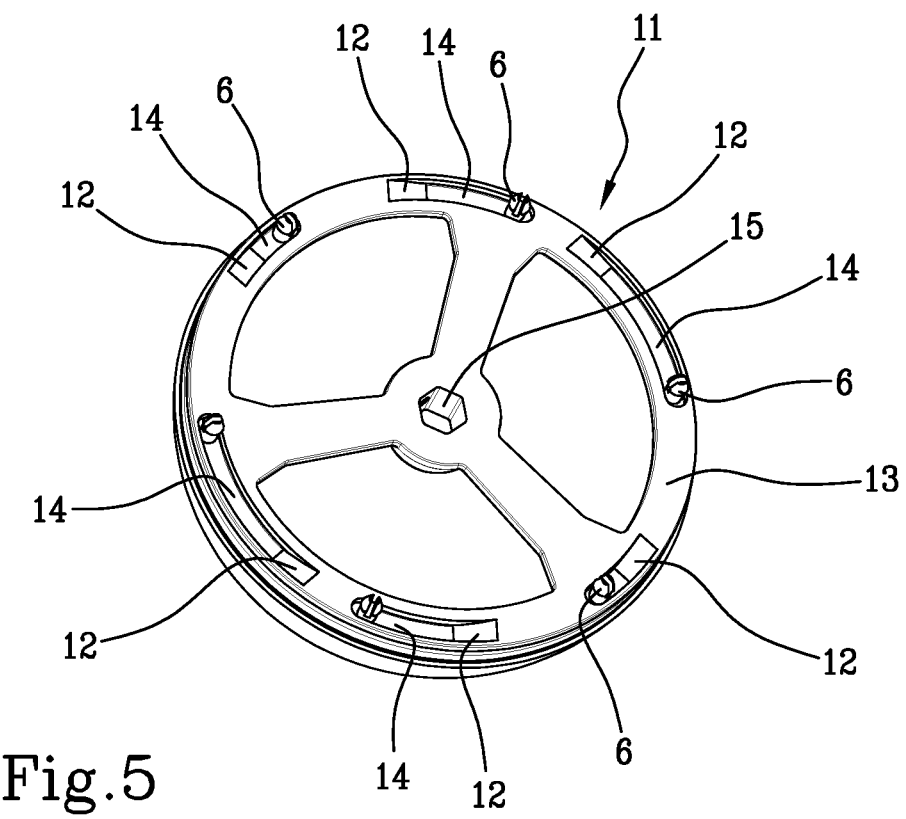
FIG. 5 is a top view of an annular body comprised within said positioning device and forming part of releasing means.

Specifically, as can be seen from FIGS. 5 and 6, these releasing means 11 comprise an annular body 13 provided with a plurality of slots 14, the number of which is equal to the number of the interlocking bonding elements 6, each equipped with a respective blade 12. Diametrically opposite pairs of slots 14 have different widths, such that the cutting of all the bonding elements 6 is not simultaneous but occurs in succession according to a predetermined sequence, preferably in pairs of diametrically opposite pins. This selective, controlled and pre-established interaction ensures a stable and continuous support for the connecting body 4 on the main body 2 of the resurfacing prosthesis throughout the step of releasing the positioning device 1 from the prosthesis, and reduces the necessary moment to be applied to the gripping and handling instrument 3 in order to achieve the cut.

The shaft coupling 41 that connects the connecting body 4 to the gripping and handling instrument 3 has a first end 41a engaged with the instrument 3 itself, and a second opposite end 41b adapted to be secured to the annular body 13 of the releasing means 11. Specifically, this second end 41b has a polygonal profile suitable to interact by mechanical interference with a corresponding polygonal through seat 15 formed centrally in the annular body 13.

Advantageously, the annular body 13 has radii that join centrally at the aforementioned polygonal seat 15.

The gripping and handling instrument 3 comprises, at a second end 3b, a knob 16 adapted to drive into rotation a shaft, not shown, which is coaxial and internal to the gripping and handling instrument 3, and directly connected with the shaft coupling 41.

Therefore, the rotary movement imparted by the knob 16 directly and exclusively activates the shaft coupling 41, which has a circular profile 41c at the circular through seat 17 of the connecting body 4, so as not to transmit any rotational movement to the latter, while it has a polygonal profile at the seat 15 of the annular body 13 of the releasing means 11, so as to give the annular body 13 a rotary movement that is independent with respect to the connecting body 4 firmly coupled to the main body 2 of the prosthesis. The blades 12 thus cut the base 6e of the pins 6, which, instead, remain stationary.

In order to proceed with the necessary surgical procedures for implanting the prosthesis, the surgeon must assemble the positioning device 1 for the positioning of a resurfacing prosthesis, object of the present invention, in a simple and quick manner.

In a first step, the surgeon acts on the gripping and handling instrument 3 in order to connect it to the connecting body 4. To do this, the surgeon acts on the button 31 by pressing it. In this way, the seat designed to receive a corresponding shaft coupling 41 of the connecting body 4 is freed, thus allowing access thereto. By releasing the button 31, a special guillotine lock mechanism (not shown) engages a respective seat provided on the shaft 41 of the connecting body 4, preventing relative translation in the axial direction between the gripping and handling instrument 3 and the connecting body 4.

As already mentioned above, relative rotation between the gripping and handling instrument 3 and the connecting body 4 is prevented by the plurality of projections 42, preferably three, which extend upwards from a surface of the connecting body 4, and are accommodated within the seat designed to receive the shaft 41.

Thereafter, the surgeon proceeds by axially aligning the assembly just created between the gripping and handling instrument 3 and the connecting body 4, with a main body 2 of a resurfacing prosthesis. Said alignment occurs such that the bonding elements 6 align with the respective recesses 7. Once the above alignment has been achieved, by axial translation, the bonding elements are forced to engage the respective recesses. This engagement takes place by forcing the bonding elements 6 to enter the respective recesses 7. As said, the shape of the bonding elements 6 is such as to prevent accidental release of the latter from the respective recesses 7. Once the pins 6 have been inserted in the respective recesses 7, by making the conical head 6b pass therethrough, the latter getting deformed during insertion, and once the head 6b itself has come out of the recess 7, by bringing the undercut 9 into abutment against the edge 10 of the recess 7, it is no longer possible to make the pins exit from the side through which they entered.

At this point, the surgeon has obtained, in a quick and simple manner, the fastening of the resurfacing prosthesis to the positioning device 1 of the present invention. It will therefore be possible to perform the necessary operations to position said resurfacing prosthesis in situ.

Once the resurfacing prosthesis has been perfectly positioned, the surgeon then proceeds by releasing said resurfacing prosthesis from the positioning device 1, object of the present invention.

To do this, the surgeon acts on releasing means 11, preferably operated by a special command positioned along the body of the gripping and handling instrument 3. In a preferred embodiment, said action entails the rotation of a special command: the knob 16. Said rotary movement, easily performed by the surgeon, sets into rotation the annular body 13 with the plurality of blades 12 thereon, adapted to cut each interlocking bonding element 6 at the respective bases. Therefore, thanks to the advantageous characteristic of the cut thus performed, the lip of the main body of the resurfacing prosthesis, at the end of the releasing operations, is smooth and free of protrusions.

The cutting action described above preferably takes place by acting on pairs of bonding elements 6. In fact, the positioning of the blades is such that, when the surgeon acts on the releasing means 11, the cutting occurs sequentially on the bonding elements 6 in pairs. In this way, advantageously, stability is maintained during the cutting of the connection between the device object of the present invention and the resurfacing prosthesis.

Therefore, the bonding elements 6 will then be cut in pairs, until the main body 2 of the resurfacing prosthesis is completely disengaged from the connecting body 4, hence from the positioning device 1.

It should be noted that, advantageously, the bonding elements 6 thus severed remain trapped inside the positioning device, in particular inside the connecting body 4, thereby preventing dispersion of foreign material inside the body of the patient, safeguarding his/her safety.

The invention described above achieves considerable advantages and allows the achievement of the intended objects.

The device object of the present invention is considerably easy to use during both positioning and removal.

This device guarantees a greater stability during impaction and ensures a stable fastening between the gripping and handling instrument and the prosthesis.

Rotational and axial stability is also guaranteed thanks to the interlocking constraint.

The described device allows the coupling of a resurfacing prosthesis for its positioning in situ during implantation, as well as the impaction thereof within the previously prepared operative site. Impaction is effective and secure thanks to the conforming surface that follows both the edge and the inner concave surface for evenly distributing the forces when the surgeon performs the impaction.

The presence of the interlocking coupling pins define a stable constraint that is not detachable, except by cutting, which ensures a firm and stable coupling once the connection between the prosthesis and the positioning device is established, conferring resistance to separation between the two components under both axial stress and bending stress, thus making the whole system integral during rotation. The surgeon can then safely go ahead with the handling of the prosthesis to place it in the operative site according to the preferred orientation.

The coupling through interlocking pins is very quick and limits the manual intervention by the surgeon who, with a simple gesture, obtains the connection of the device to the prosthesis.

The disengagement of the positioning device from the prosthesis is also quick and safe: a simple rotation of a portion of the gripping and handling instrument activates a cutting mechanism that, in a simple, calibrated and safe way releases the device from the prosthesis, without causing further stress on the already positioned prosthesis and avoiding any risk of misalignment thereof within the operative site.

The device object of the present invention also has a limited number of components, which certainly facilitates its use.

In fact, only one plate or connecting body is used for positioning, impacting and removing. Furthermore, once the cut pins have been removed, the connecting body can be re-used for other operations.

The method of assembling the device and the corresponding method of releasing it from the main prosthesis body is extremely quick, simple and limits manual intervention.

The invention claimed is:

1. A device for positioning a resurfacing prosthesis comprising:
   a gripping and handling instrument for a main body of a resurfacing prosthesis;
   a connecting body interposed between said gripping and handling instrument and said main body of said resurfacing prosthesis and suitable to connect them; and
   a coupler which secures said connecting body to said main body, said coupler comprising:
      a plurality of interlocking pins protruding axially from a lip of said main body and adapted to be each interlocked in an irremovable manner in a respective through hole provided in said connecting body; and
      a shear releaser interposed between said main body of said resurfacing prosthesis and said connecting body, the shear releaser adapted to detach said connecting body from said main body,
      wherein said shear releaser acts directly on said interlocking pins for separating said interlocking pins from the main body of the prosthesis by cutting said pins at their respective base so that, after being cut, the main body has a completely smooth and levelled lip.

2. The device according to claim 1, wherein said releaser comprises a plurality of blades operated when the gripping and handling instrument or a portion thereof is made to rotate.

3. The device according to claim 2, wherein said plurality of blades act consecutively and selectively on the interlocking pins, said interlocking pins being arranged diametrically opposite one another with respect to an axis of symmetry of said connecting body so as to provide a stable and continuous support between the main body and the connecting body during a removal step and to reduce the necessary moment to be applied to the connecting body.

4. The device according to claim 1, wherein said releaser acts consecutively and selectively on a limited number of the interlocking pins, the interlocking pins arranged diametrically opposite one another with respect to an axis of symmetry of said connecting body so as to provide a stable and continuous support between the main body and the connecting body during a removal step and to reduce the necessary moment to be applied to the connecting body.

5. The device according to claim 1, wherein said releaser comprises an annular body provided with a plurality of slots the number of which is equal to the number of interlocking pins, said plurality of slots being each provided with a blade; said slots differing in size but with diametrically opposite pairs being of the same size such that the cutting of the interlocking pins is not simultaneous but occurs in succession according to a predetermined sequence.

6. The device according to claim 1, wherein said interlocking pins have a change in diameter along their axial length and an undercut suitable to abut on an edge of the respective through hole in said connecting body.

7. The device according to claim 6, wherein said interlocking pins comprise a cylindrical shank and a conical head having a base diameter greater than a diameter of the cylindrical shank and an axial slot to permit the deformation thereof during a step of insertion into the respective through hole to facilitate coupling.

8. A method of assembling a device for the positioning of a resurfacing prosthesis, the method comprising the steps of:
   connecting a gripping and handling instrument to a connecting body;
   axially aligning a main body of a resurfacing prosthesis with said connecting body so that interlocking pins protruding from a lip of said main body are aligned with respective through holes obtained in the connecting body;

acting on said gripping and handling instrument to enable insertion of said interlocking pins into said through holes so as to secure said main body to said connecting body in an irremovable manner; and activating a shear releaser interposed between said main body of said resurfacing prosthesis and said connecting body, wherein the activating cuts each of the interlocking pins and releases said connecting body from said main body.

9. The method according to claim 8, wherein the shear releaser comprises a plurality of blades suitable to cut each of the interlocking pins at its respective base so that the lip of the main body of said prosthesis remains smooth and devoid of protrusions.

10. The method according to claim 9, wherein the step of activating the shear releaser comprises consecutively and selectively cutting a limited number of the interlocking pins at a time.

* * * * *